US009180043B2

(12) United States Patent
Merrill et al.

(10) Patent No.: US 9,180,043 B2
(45) Date of Patent: Nov. 10, 2015

(54) APPARATUS FOR TREATMENT OF REPERFUSION INJURY

(75) Inventors: Denise R. Merrill, Sewell, NJ (US); Todd J. Nilsen, Howell, NJ (US); Jennifer Ellen Akers, Elmer, NJ (US); Kyle Stever, Huntsville, AL (US); Moshe Laifenfeld, Haifa (IL); Ravi Ramachandran, Turnersville, NJ (US)

(73) Assignee: Focal Cool, LLC, Sewell, NJ (US)

( * ) Notice: Subject to any disclaimer, the term of this patent is extended or adjusted under 35 U.S.C. 154(b) by 1030 days.

(21) Appl. No.: 13/297,048

(22) Filed: Nov. 15, 2011

(65) Prior Publication Data

US 2012/0123509 A1 May 17, 2012

Related U.S. Application Data

(60) Provisional application No. 61/456,908, filed on Nov. 15, 2010.

(51) Int. Cl.
*A61F 7/12* (2006.01)
*A61F 7/00* (2006.01)
*A61B 17/00* (2006.01)

(52) U.S. Cl.
CPC ................ *A61F 7/12* (2013.01); *A61F 7/0085* (2013.01); *A61B 2017/00084* (2013.01); *A61F 2007/0056* (2013.01); *A61F 2007/0095* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,333,614 | A * | 8/1994 | Feiring | 600/466 |
| 6,033,383 | A | 3/2000 | Ginsburg | |
| 6,645,234 | B2 | 11/2003 | Evans et al. | |
| 2004/0167467 | A1 | 8/2004 | Harrison et al. | |
| 2004/0181206 | A1* | 9/2004 | Chiu et al. | 604/509 |
| 2006/0041217 | A1 | 2/2006 | Halperin et al. | |
| 2006/0058859 | A1 | 3/2006 | Merrill | |

* cited by examiner

*Primary Examiner* — Joseph Stoklosa
*Assistant Examiner* — Adam Avigan
(74) *Attorney, Agent, or Firm* — Mark Books

(57) ABSTRACT

An apparatus to minimize and/or eliminate the effects associated with reperfusion injury consisting of an external pump, heat exchanger and control unit creating a flow loop whereby blood is moved from the body via a pump, cooled by an external heat exchanger and reintroduced into a specific location, thereby locally cooling the surrounding tissue and inducing localized hypothermia to minimize tissue injury resulting from ischemia and the effects associated with reperfusion injury as an obstruction is removed and normal blood flow is restored and including the ability to locally measure pressure and temperature in the body.

16 Claims, 10 Drawing Sheets

FIGURE 13
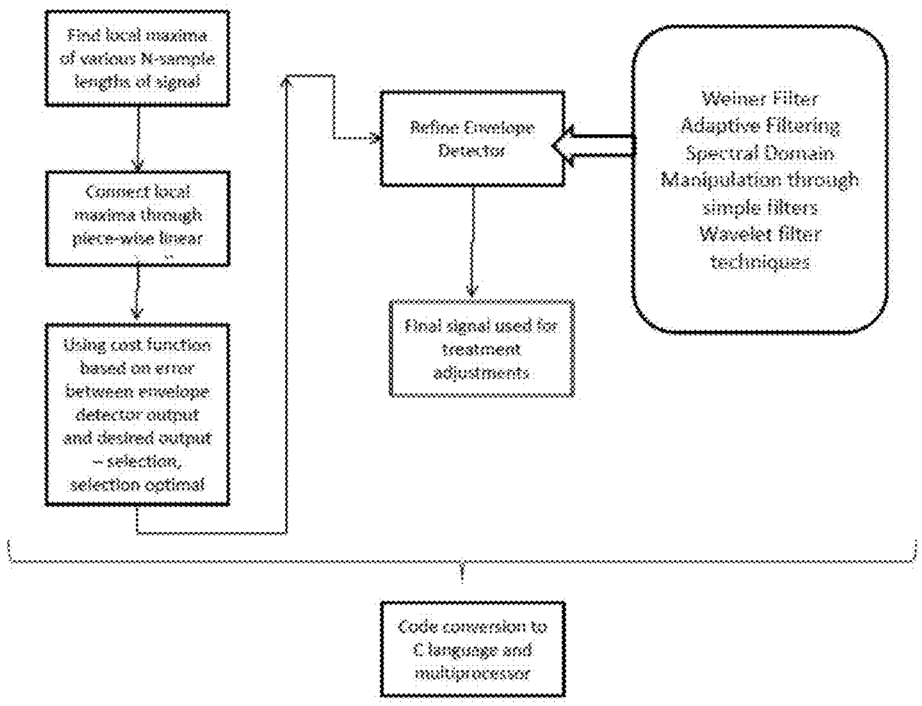
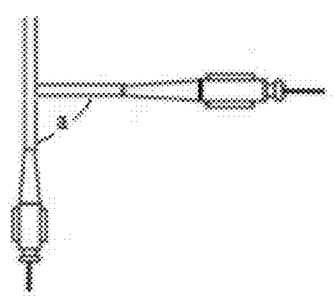
FIGURE 14

APPARATUS FOR TREATMENT OF REPERFUSION INJURY

CROSS-REFERENCE TO RELATED APPLICATIONS

The present application is related to and claims priority from U.S. Provisional Patent Application Ser. No. 61/456,908, filed on Nov. 15, 2010, the entire contents of which are herein incorporated by this reference

STATEMENT REGARDING FEDERALLY SPONSORED RESEARCH

The National Institute of Health provided support for the subject matter of this patent application under Grant #1 R43 NS073291-01 (A combination endovascular device: thrombectomy with localized hypothermia) and the United States government may have certain rights in this application.

BACKGROUND OF THE INVENTION

The present invention relates generally to an apparatus and method for minimizing the effects of ischemia and the subsequent injury upon reperfusion of organs and/or tissue masses resulting from minimal to total obstructions of normal blood flow. This is achieved by the integration of a pump, heat exchanger and control unit providing the ability to locally cool a part of the anatomy inducing local hypothermia and minimizing and/or eliminating the injury associated with ischemia and subsequent reperfusion.

When a patient comes into the emergency room showing signs of a stroke or heart attack, three options for treatment are available: pharmacological intervention (i.e., the use of thrombolytics), invasive surgery or minimally invasive treatment to eliminate or lessen an obstruction in a coronary vessel. Catheter based treatments have become the standard care path for the diagnosis and treatment of strokes or acute myocardial infarction (AMI). Studies have shown that a significant amount of tissue damage occurs due to the reperfusion of warm blood into the previously occluded vessels.

The total extent of tissue injury and the amount attributed to either the ischemic event or reperfusion is unknown. However, localized cooling has been shown to both reduce tissue injury during ischemia and the amount of injury resulting from reperfusion of the tissue. Reperfusion injury is caused by an immediate increase in rapid flow of blood into an organ or tissue mass previously rendered ischemic and is attributed to oxidative stress, intercellular calcium overload, neutrophil and platelet activation, reduced microvascular flow, metabolic disturbances, the buildup of toxins in the tissue and inflammatory reactions. Renewed normothermic blood flow worsens tissue damage either by causing additional injury or by unmasking injury sustained during the ischemic period. Thus, early treatment of an obstruction, for example in the heart using percutaneous coronary intervention, is desirable. Once the obstruction is alleviated normothermic blood flow is restored to the ischemic region resulting in a reperfusion injury.

Experimental evidence has shown that reductions in tissue temperature can reduce the effects of ischemia, reperfusion injury, or inadequate blood flow. Among other mechanisms, hypothermia decreases tissue metabolism, concentrations of toxic metabolic byproducts, and suppresses the inflammatory response in the aftermath of ischemic tissue injury. Mild cooling of the tissue region by a temperature of as little as 3-4° C. below normal body temperature may provide a protective effect with the increase in protection/reduction in injury directly associated with the decrease in temperature of the organ or tissue effected by the ischemic event. Hypothermia has been shown to drastically reduce oxygen free radical production and intercellular calcium overload, platelet aggregation, the occurrence of microvascular obstruction, metabolic demand, and inflammatory response in the aftermath of ischemic tissue injury. Hypothermia may provide ischemic protection and may enhance patient recovery by ameliorating secondary tissue injury. Depending on the time of initiation, hypothermia can be intra-ischemic, post-ischemic, or both. Hypothermic ischemic protection is preventive if tissue metabolism can be reduced. It may also enhance recovery by reducing secondary tissue injury or decreasing ischemic edema formation. Since the metabolic reduction is less than 10% per degree Celsius, deep hypothermia targeting 20-25 degrees Celsius, provides adequate tissue protection via metabolic slowdown. Secondary tissue injury, thought to be mainly caused by enzymatic activity, is greatly diminished by mild to moderate hypothermia targeting 32-35 degrees Celsius.

Not only can hypothermia be protective for the unexpected onset of ischemia it can be used prophylactically where surgical intervention/medical therapy will cause a known ischemic event (e.g., cardiac bypass and organ transplant surgery). To harness the therapeutic value of hypothermia the primary focus thus far has been on systemic body surface or vascular cooling. Systemic cooling has specific limitations and drawbacks related to its inherent unselective nature. Research has shown that systemic or whole body cooling may lead to cardiovascular irregularities such as reduced cardiac output and ventricular fibrillation, an increased risk of infection, and blood chemistry alterations.

In practice, systemic cooling apparatus and their associated methods require long periods of time to achieve target tissue temperatures causing damage along the way. External cooling devices have been used as adjunct therapy for cardiac arrest where the goal is to salvage brain tissue and improve neurological outcomes. Many systemic cooling systems require the movement of large volumes of blood flow to the brain and cooling is achieved by diluting blood with infusion of cold fluids. In general, these devices and their associated methods are not applicable to localized cooling to reduce reperfusion injury in specific organs or tissue masses. To date localized cooling techniques have been defined by placement of an ice pack over the particular area of a patient's body and puncturing the pericardium and infusing cooled fluid into a reservoir inserted into the pericardial space near the ischemic cardiac tissue.

Few concepts have attempted local, organ specific cooling. Local cooling approaches have been limited by the technological challenges related to developing catheter systems including internal heat exchangers and the reliability and safety associated with their use. Namely, without a control feedback loop monitoring physiological conditions at the treatment location and adjusting the cooling the ability to repeatedly and continually induce specific localized cooling parameters is random at best and lacks the accuracy and repeatability required in providing medical treatment. An advantage of local or organ level cooling is the reduced thermal inertia, since the cooling capacity required is directly proportional to the mass being cooled. Cooling a portion of a 300 gram heart vs. a 70,000 gram body of a patient takes significantly less cooling capacity to reach equivalent reduced temperatures.

While hypothermia technologies have been progressing, the fields of endovascular intervention and minimally invasive surgery have also grown. Today therapeutic devices include stent placement, angioplasty, direct thrombolytic infusion, and mechanical devices for clot removal. In each of these therapeutic environments, ischemic damage is the focus. To accomplish this however, requires an integrated cooling system that not only offers the ability to cool but also can monitor physiological conditions at a specific location in the body. Monitoring the physiological conditions facilitates local cooling of an organ or tissue mass by accommodating heat loss along the length of a catheter, regulating local pressure changes, and provide a sustained environment while adjunct therapy is administered and normal blood flow is restored. Heat transfer enhancement is the fundamental task for achieving safe, effective arterial cooling. Monitoring the conditions at the specific cooling site permits the system to achieve the highest level of cooling capacity in the smallest volume possible. Heat exchanger design optimization attempts to achieve one or a combination of the following objectives: 1) reduce the size of the transport device; 2) increase the UA (U, the overall transport coefficient and A, the exchange surface area) to reduce the device-body fluid driving potential for exchange or increase the heat and or mass exchange rate; and 3) reduce the pumping power required to meet a heat and/or mass exchange target value.

Most endovascular cooling catheter designs employ external passive transport enhancement techniques, where a fixed or static cooling catheter is placed inside a stagnant or moving body fluid. Passive techniques are transport enhancement approaches that do not add mixing energy to the fluid system of interest. The approach involves adding surface area and/or inducing turbulence adjacent to the effective exchange surface area. They are particularly effective when fluid pumping power is virtually limitless. In the human body, however, physiological constraints limit the hydraulic energy or fluid pumping power. As a result, passively enhanced devices in small arterial vessels are likely lead to substantial blood side flow resistance, diminishing organ perfusion levels.

In general, current designs are suited for the venous system, a system with large veins, significantly larger than small arteries. In this environment most of devices have low heat exchange surface area to device volume ratios. This leads to potentially harmful vessel occlusion characteristics, particularly with smaller arterial blood vessels, increasing the chance of further ischemic injury. Unless additional energy is put into the blood flow stream, conservation of energy dictates that in most cases a boost in heat transfer will come at an increased cost in pressure drop. If the cardiovascular system cannot overcome this additional foreign resistance, perfusion rates must fall.

Furthermore traditional catheters do not have dedicated adjunctive therapy pathways. Again, the catheter designs are built largely for the venous applications where adjunctive therapies are less likely. As a result, these designs do not integrate well with existing endovascular tools, such as angioplasty catheters. Although present devices are functional for venous applications, they are not sufficient for arterial applications. Accordingly, a system and method are needed to address the shortfalls of present technology and to provide other new and innovative features.

United States Patent Application Publication No. 2006/0041217 to Halperin discloses the use of a controller applying an algorithm to maintain a predefined infusion pressure, however the controller is limited to systemic pressure alone and does not provided feedback of the local environment where the ischemic event and reperfusion have occurred. Hence the Halperin disclosure does not control the safe application of cooled fluid within the body inducing localized hypothermia.

However, taking blood from the body cooling it and redelivering it within a specific location with control feedback and localized monitoring used in conjunction with interventional devices (stents, angioplasty balloons, etc.) provides a safe and effective means of inducing localized hypothermia to minimize the negative effects associated with temporary ischemia and injury upon reperfusion in a controlled manner.

There are several designs available for a small artery cooling catheter, such as shown in U.S. Patent Application Publication No. 2006-0058859 A1 to Merrill, which is herein incorporated by reference. Some catheter configurations define an exchange catheter with heat and mass exchange surfaces, some define a transport catheter to carry the coolant, and some include a rear external hub to connect the device to an outside control console and engage adjunctive therapeutic devices. One particular cooling catheter configuration uses natural pressure differences between the aorta and the end organ to carry blood inside the cooling catheter.

Traditional devices as taught in U.S. Pat. No. 6,033,383 to Ginsburg and U.S. Pat. No. 6,645,234 to Evans cool blood as a function of heat transfer from a coolant which is delivered within a catheter and provided in close contact with the flowing blood. In other words the blood is cooled as it flows past and/or through a catheter based device having a cooling element contained within its construction. These types of devices do not provide sufficient control so that the specific organ or tissue mass is cooled sufficiently to produce localized hypothermia. Additionally, the multi-lumen designs of Ginsburg and Evans required to provide paths for coolant, blood, and any interventional procedures results in a large external diameter of roughly 8 French. In addition, the pressure differential provided by the normal circulation of blood may not be sufficient to direct flowing blood in a manner required to optimize heat transfer and induce localized hypothermia.

Conversely, a completely external cooling system with sufficient controls and feedback is better able to integrate into the current treatment modality for ischemic conditions (e.g., stents, balloon angioplasty, clot removal devices) and the subsequent reperfusion. United States Patent Application US 2004/0167467 to Harrison et al. discloses a localized cooling method containing a temperature probe within the distal end of the catheter measuring the temperature of the fluid exiting the catheter. However, the temperature probe is not operatively connected to the heat exchanger, and there is no control unit monitoring and adjusting the flow rate, amount of cooling, or the localized pressure to provide a safe and efficacious supply of localized cooled fluid controlled per the users specifications before, prior to, and after an ischemic event.

Accordingly, it would be advantageous to provide an apparatus to facilitate the localized cooling of a flow of blood to a specific region or organ of a patient's body as an adjunct to interventional therapy lessening reperfusion injury, and which is configured with a feedback control system to monitor and adjust both the temperature and pressure of the cooling flow of blood and to monitor the patient's internal temperatures and blood pressures to ensure patient safety.

It would further be advantageous to provide a cooling system capable of delivering cold blood to a treatment site while allowing a physician to use familiar catheters and interventional tools.

BRIEF SUMMARY OF THE INVENTION

In a first embodiment, the present disclosure sets forth an apparatus configured to minimize and/or eliminate the effects associated with reperfusion injury. The apparatus consists of an external pump, a heat exchanger, and a control unit creating a flow loop whereby blood is moved from a patient's body through a catheter via the external pump, cooled by the heat exchanger, and reintroduced into a specific location within the patient's body through the catheter, thereby locally cooling the surrounding tissue or organs. The flow of cooled blood is regulated by the control unit to induce localized hypothermia, thereby minimizing tissue injury resulting from ischemia and the effects associated with reperfusion injury until normal blood flow is restored. The control unit is operatively coupled to temperature and pressure sensors within the catheter to locally measure pressures and temperatures within the body of the patient during the procedure, and to regulate the flow of cooled blood as necessary for the safety of the patient using a feedback control loop, avoiding ventricularization, and dampening.

In one embodiment, the apparatus further includes a bubble sensor contacting the outside of the tubing in which the fluid flows and external to the patient. The bubble sensor is operatively coupled to the control unit and detects the presence of bubbles within the flowing fluid in the flow loop. The output from the bubble sensor is continually monitored by the control unit, enabling the detection of the presence of bubbles within the system and automatically ending the fluid flow.

In one embodiment, the catheter of the apparatus is a specialized internal cooling catheter incorporating cooling elements (e.g. thermoelectric semiconductors, Joule-Thompson orifice) located near the distal tip.

In one embodiment, the control unit is configured to achieve the desired local temperature within a selected region of a patient's body tissue or organ by adjusting the rate of blood delivered and the amount of cooling while taking into account the loss of cooling (i.e., increase in temperature) as blood moves through the delivery catheter to a specific location within the patient's body and the local pressure and temperature at the treatment site.

BRIEF DESCRIPTION OF THE SEVERAL VIEWS OF THE DRAWINGS

FIG. 13 shows a non-limiting flowchart of the envelope detector algorithm;

FIG. 14 shows an embodiment of the hub 12 in an alternate configuration.

DETAILED DESCRIPTION

The figures and their detailed description are not intended to limit the scope of the invention but to provide an overview of its various features connections and operation in one or more non-limiting embodiment.

Within the present disclosure the term "fluid" is used generically and refers specifically to blood from the patient, donor blood, artificial blood substitutes, saline, human albumin and all other substances able to be introduced into the body as is necessitated by the procedure.

Within the present disclosure the term "obstruction" refers to a complete or partial interruption within the pathway of a body passage. For example, obstruction can refer to an artery completely occluded by a clot or embolic particle or a partial reduction in luminal diameter resulting from a narrowing of a blood vessel.

Figure 1:
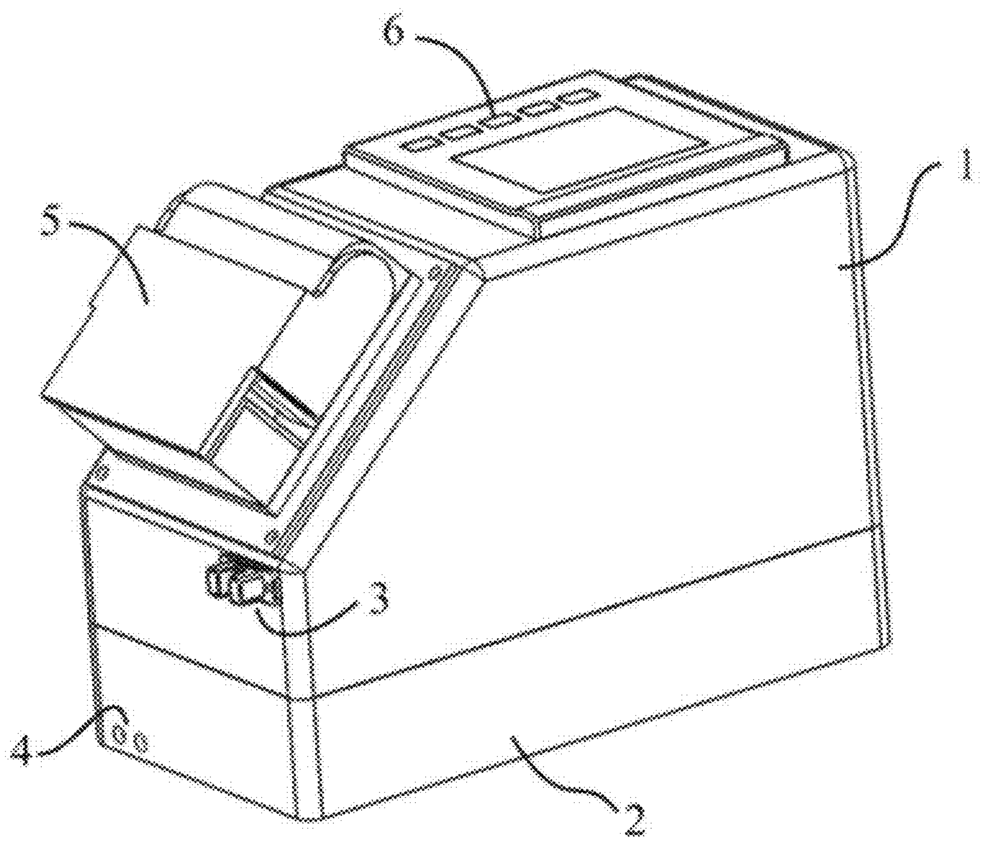
FIG. 1 shows an isometric view of a cooling system of the present disclosure.

Referring to FIG. 1 an isometric view of the cooling system of the present disclosure including a housing 1, control module 6, pump 5, housing base 2, fluid connection input and exit ports 4 for the supply of fluid to the unit and return of cooled fluid to the patient, and monitoring inputs 3 for gathering local temperature and pressure at the desired treatment location. The power supply input or an internal power supply is not shown. The housing 1 and the housing base 2 are composed of one or more materials able to withstand exposure to corrosive fluids (e.g., blood, saline) and able to be covered with disposable plastic shields. Preferably, the housing and housing base are adapted to be positioned on a catheter lab table, mounted to a pole, or secured to the catheter lab table.

Components internal to the housing base 2 utilized for cooling fluid and exposed to body fluids can be either disposable or able to be re-sterilized within a hospital setting. Tubing (not shown) used to transmit the force of the pump 5 to fluid within a tube connected to the patient, to drive the fluid into the housing base 2, and to re-circulate the flow of fluid to the patient are preferably disposable or able to be re-sterilized within the hospital setting. Optionally, the tubing is configured to connect to any standard medical equipment available in a lab or medical facility via luer fittings. The monitoring inputs 3 are attached to single use probes, or to probes able to be re-sterilized and intended to be placed within the treatment location within the patient.

During operation the fluid tubing (not shown) is connected to a reservoir of fluid or a port connected to the patient. The fluid tubing is then inserted through the pump 5 and connected to the input port of the cooling chamber 4, located within the housing base 2. A return path of fluid tubing exits the cooling chamber 4 and is then reconnected to a catheter based device 9 for placement in the patient, at or in close proximity to the location of the ischemic event or organ where cooling is desired.

Figure 2:
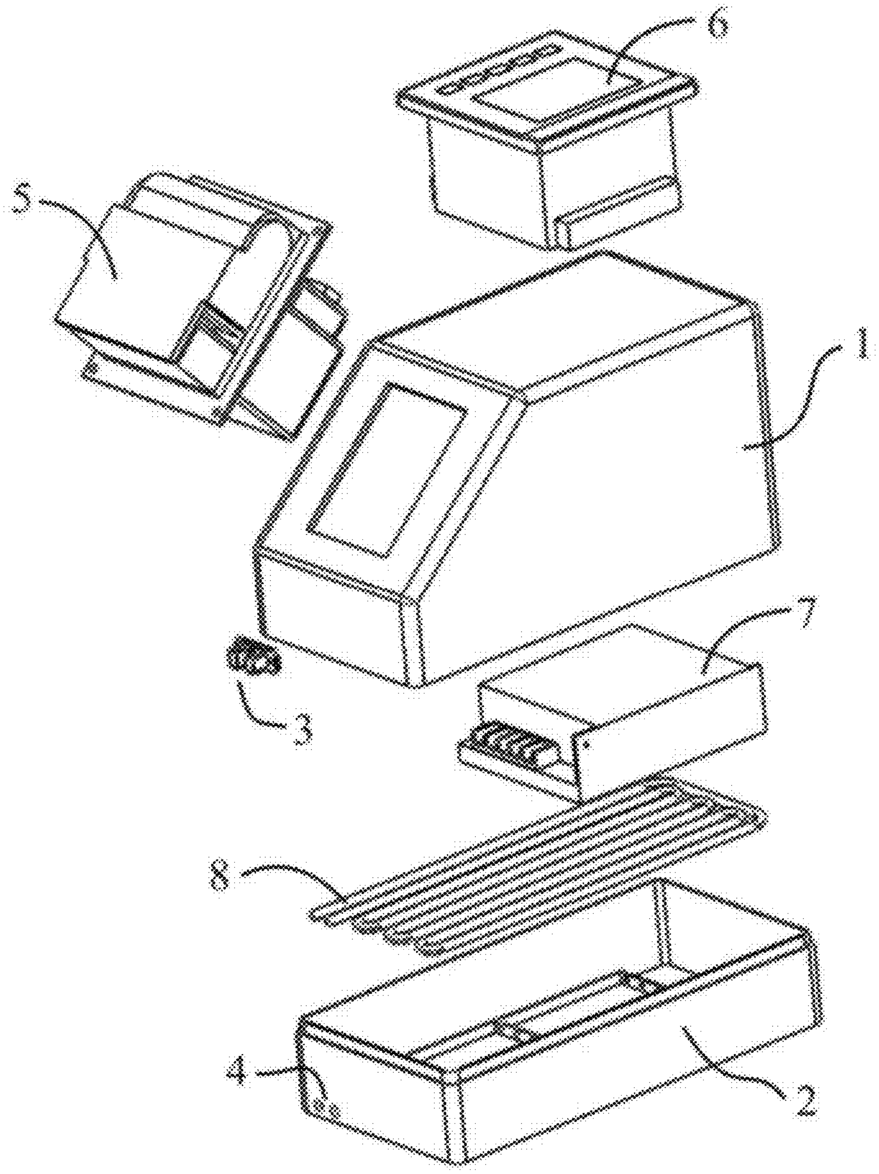
FIG. 2 shows an exploded view of the cooling system of FIG. 1.

Referring to FIG. 2 an internal control unit 7 contained within the housing 2 is operatively connected to the external control panel to define a control module 6, and to the cooling coil 8. The control unit 7 monitors the local pressure and temperature within the patient, and utilizes the monitored pressure and temperature in a feedback loop to adjust the flow of fluid driven by the pump 5 and the amount of cooling delivered to the fluid flow by the cooling coil 8. Alternatively, the pressure can be determined by the control unit 7 at the fluid exit of the cooling coil 8 using signal processing algorithms to decouple the patient's native cardiac pressure level and the introduced pump pressure level of the apparatus. The control unit 7 is further responsive to user inputs and safety controls to ensure the desired parameters are achieved at the treatment location within the patient while not compromising patient safety.

Those of ordinary skill in the art will recognize that the cooling coil 8 as shown in FIG. 2 may be replaced by a disposable heat exchanger that is filled with ice mold packages frozen into ice blocks before use, or alternatively, can be replaced by a heat exchanger connected to a reusable chiller device.

Figure 3:
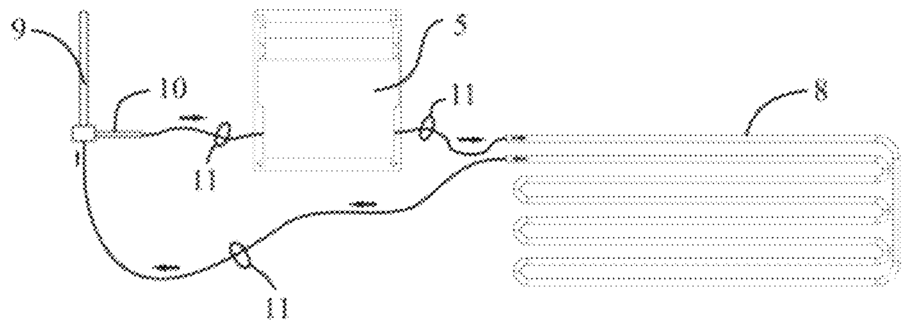
FIG. 3 shows a directional path of fluid being retrieved from the patient and recirculated making use of a catheter based delivery method.
Figure 4:
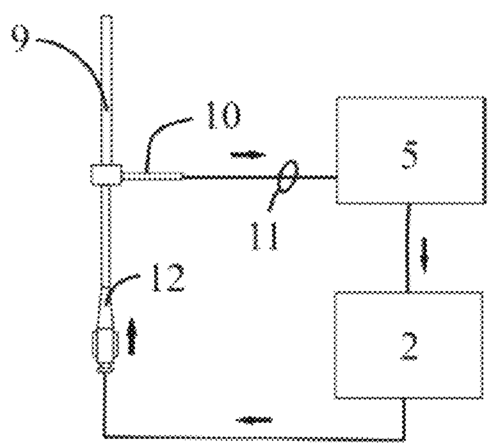
FIG. 4 shows a directional schematic of fluid being retrieved from the patient cooled and recirculated making use of a catheter based delivery method.

Referring to FIG. 3 a schematic of the flow of cooling fluid is shown exiting from an exit port 10 connected to, or placed in tandem with, the catheter based device 9. The fluid flows from exit port 10 through fluid tubing 11 to the pump 5, which provides a pressure differential to drive the flow of fluid from the exit port 10 through the cooling apparatus. As the flow of fluid exits the pump 5 it flows through the cooling coil 8 and is re-circulated to the treatment site within the patient via the catheter based device 9 located proximal to the ischemic obstruction or organ to be cooled. FIG. 4 illustrates the same schematic is shown as in FIG. 3, but with a higher level of abstraction, showing the housing base 2 and catheter hub 12.

Figure 5:
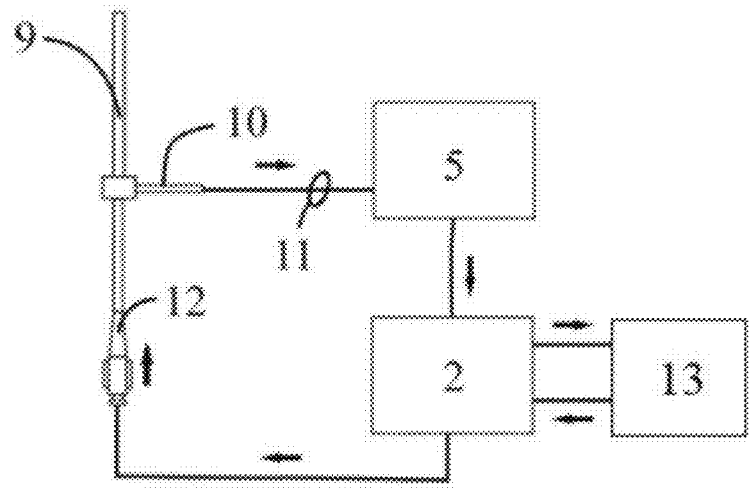
FIG. 5 shows a directional schematic of fluid being retrieved from the patient cooled and recirculated making use of a catheter based delivery method where the cooling of the fluid is aided by the delivery of cooled fluid and removal of warm fluid by means of a chiller contained within the cooling system of FIG. 1.

Referring to FIG. 5, an alternate embodiment is shown whereby the flow of fluid within the cooling coil 8 located within housing base 2 is further cooled by use of an additional chiller 13. Chiller 13 provides additional cooling to the flow of fluid entering the patient's body through the catheter based device 9 by way of catheter hub 12.

Figure 6:
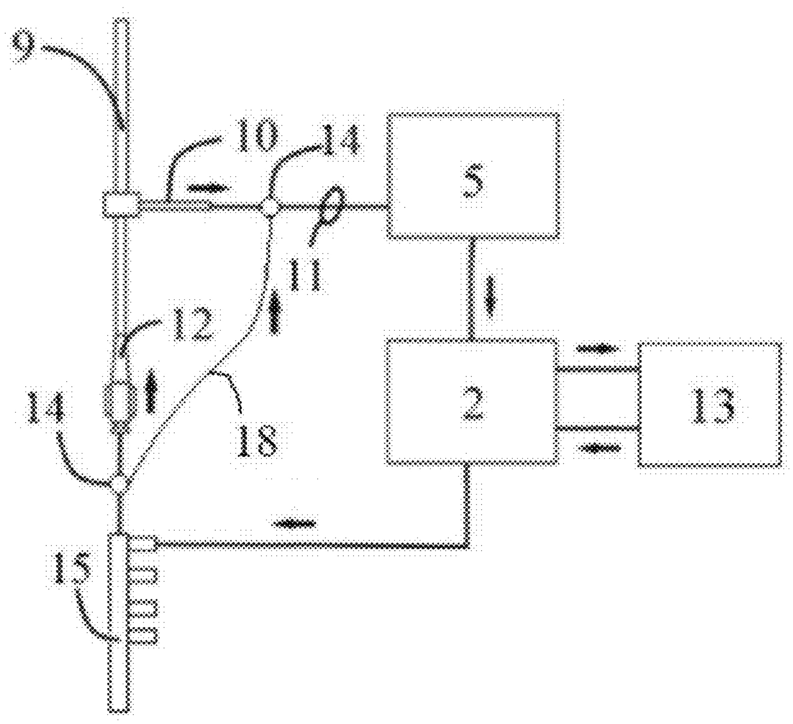
FIG. 6 shows a directional schematic of fluid being retrieved from the patient cooled and recirculated making use of a catheter based delivery method attached to a manifold where the cooling of the fluid is aided by the delivery of cooled fluid and removal of warm fluid by means of a chiller contained within the cooling system of FIG. 1 and containing a recirculation shunt to redirect bypass reintroduction of the cooled fluid back into the patient.

Referring to FIG. 6 an alternate embodiment is shown whereby a manifold 15 is used in the flow of fluid in conjunction with the apparatus and a bypass fluid path 18 controlled by valve 14. The manifold 15 receives and delivers fluid into the catheter based device 9 by way of the catheter hub 12. In the event the user wishes to discontinue the flow of fluid into the patient's body, the valve 14 is closed and the fluid directed back through the bypass fluid path 18, thereby bypassing the patient and the catheter based device 9. The manifold 15 can be used to deliver additional fluids (e.g., contrast media, saline) into the catheter based device 9 without requiring disconnection of the cooling apparatus.

Figure 7:
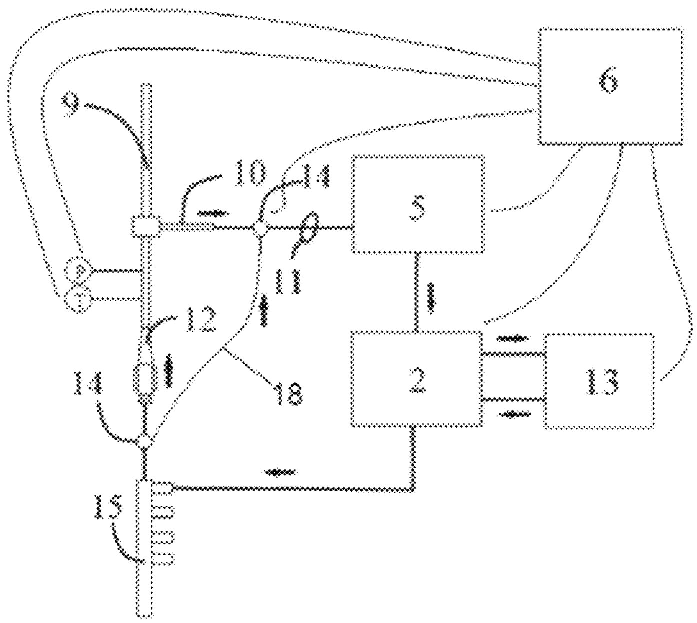
FIG. 7 shows a control unit incorporated within the schematic of FIG. 6.
Figure 15:
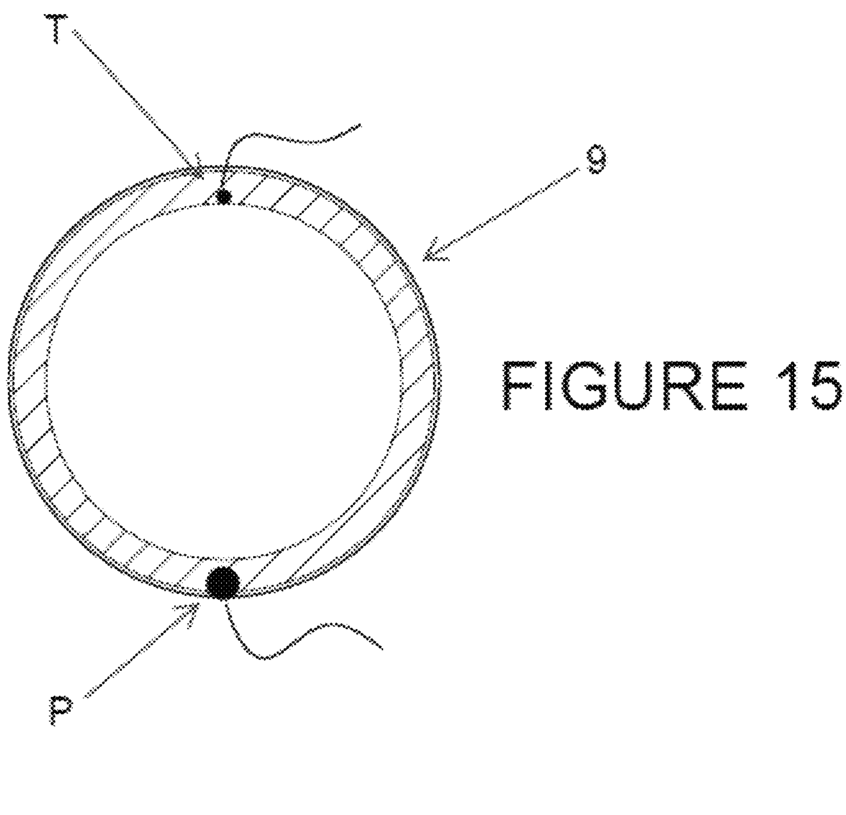
FIG. 15 shows a cross sectional view of the distal end of an exemplary cooling catheter, incorporating both pressure and temperature sensors.

Referring to FIG. 7 the control module 6, including the control unit 7, is depicted as being operatively connected to the functional aspects of the apparatus of the present disclosure. In this embodiment the control module 6 monitors the pressure P and temperature T acquired at the treatment location by probes placed within the distal tip of the catheter based device 9, as seen in FIG. 15. The probes may be permanently installed within the structure of the catheter based device 9, or may be of a temporary nature. Alternatively, the pressure P and temperature T may be monitored by calculations based on the algorithms used to program the control module 6 or by a combination of algorithms and probes. Based on user inputs, pressure P, and temperature T, the control module 6 is configured to adjust the operation of the pump 5, the cooling coil 8, the chiller 13 (if present), and the bypass valve 14 to ensure the safe operation of the cooling apparatus such that the desired temperature fluid is delivered at the treatment location to minimize the effects associated with ischemia and reprofusion.

Figure 8:
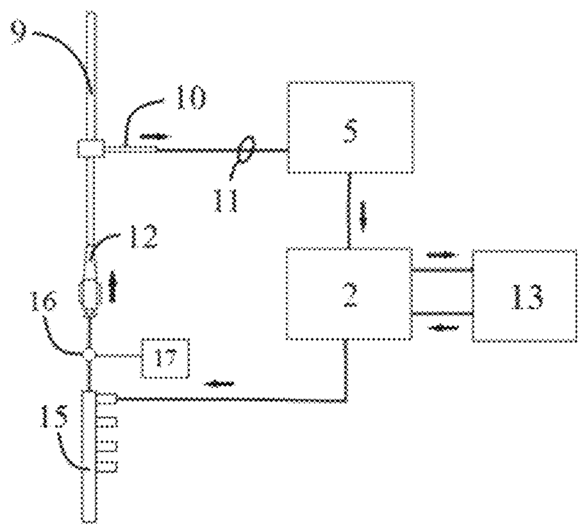
FIG. 8 shows a directional schematic of fluid being retrieved from the patient cooled and recirculated making use of a catheter based delivery method attached to a manifold where the cooling of the fluid is aided by the delivery of cooled fluid and removal of warm fluid by means of a chiller contained within the cooling system of FIG. 1 and containing a purge mechanism to purge fluid from the lines under certain circumstances.

Referring to FIG. 8, in alternate embodiment of the cooling apparatus, the bypass fluid path 18 and the valve 14 are removed and replaced with a purge valve 16 and a purge mechanism 17 used to purge fluid from the lines when there is an issue with the safe operation of the cooling apparatus or when it is no longer desired to deliver fluid into the catheter based device 9.

One issue with the safe operation of the cooling apparatus can be the presence of air within the fluid lines 11, or the formation of a clot when blood is used as the cooling fluid. The presence of air or a clot can be as detected by the control module 6 as a change in fluid viscosity, as a change in internal pressure within the fluid flow, or as a change in the pumping requirements to move the fluid within the fluid lines 11. The purge mechanism 17 has the ability to both purge fluid from the lines and to replace purged fluid with fresh fluid from a secondary reservoir (not shown).

Figure 9:
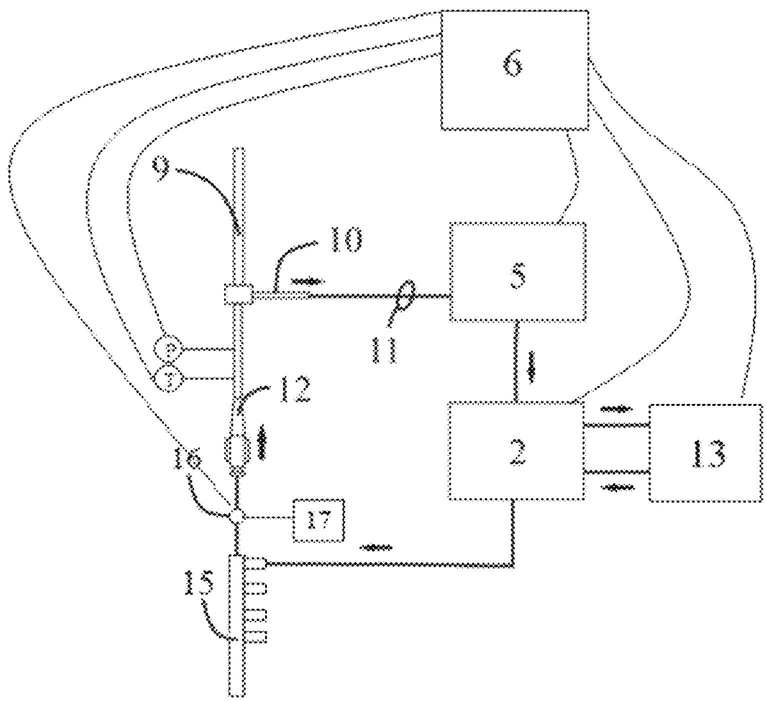
FIG. 9 shows a control unit incorporated within the schematic of FIG. 8.

Referring to FIG. 9 the control module 6 is depicted as being connected to the functional aspects of the device. In this embodiment the control module 6 monitors the pressure P and temperature T acquired at the treatment location by probes placed within the distal tip of the catheter based device 9. The probes may be permanently installed within the catheter based device 9, or may be of a temporary nature. Alternatively, the pressure P and temperature T may be monitored by calculations based on the algorithms used to program the control module 6 or by a combination of algorithms and probes. Based on user inputs, the pressure P, and the temperature T, the control module 6 adjusts the operation of the pump 5, the cooling coil 8, the chiller 13 (if present), and purge valve 16, and a purge mechanism 17 to ensure the safe operation of the cooling apparatus such that the desired temperature fluid is delivered at the treatment location to minimize the effects associated with ischemia and re-profusion.

Figure 10A:
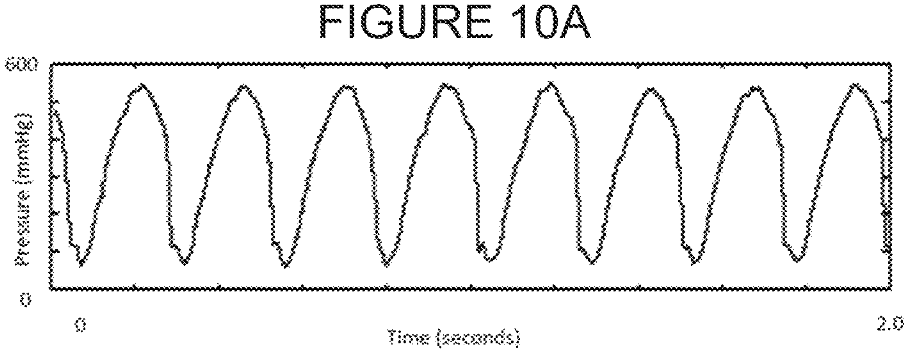
FIGS. 10A-10C show an example of pressure waveforms present during operation: coronary blood pressure, peristaltic blood pump pressure, and the composite wave form that is created when these two waveforms are combined depicted as frequency domain plots from in vitro data: coronary pressure inside the heart (10A), blood analog pressure in the catheter (10B), and the combined waveforms (10C)
Figure 10B:
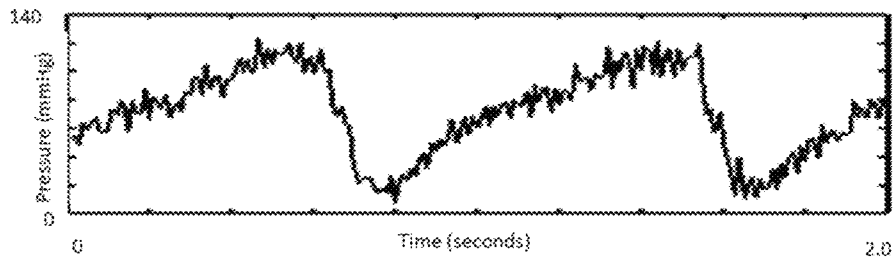
Figure 10C:
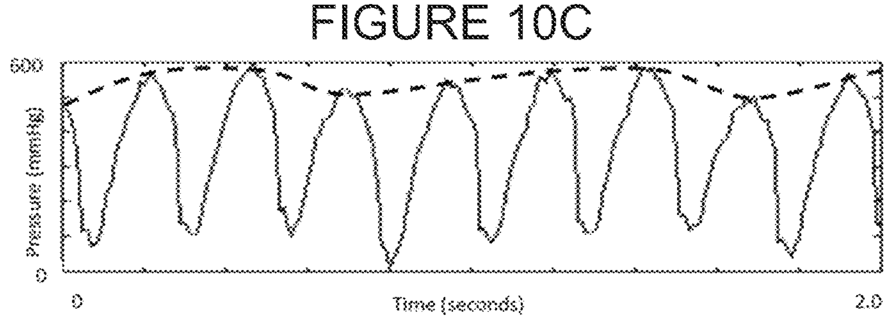

Referring to FIGS. 10A-10C, exemplary illustrations of pressure waveforms present during operation of the cooling apparatus are shown. FIG. 10A illustrates peristaltic blood pump pressure, FIG. 10B illustrates coronary blood pressure, and FIG. 10C illustrates a composite wave form that is created when these two waveforms are combined. The peristaltic blood pump pressure and coronary blood pressure signals are combined to form the composite wave form signal. The modulating signal is considered to be a message signal. The control module 6 is configured with envelope detecting algorithms to extract the dashed waveform from the composite wave form that reveals the message. The detecting algorithms seek blind separation of the blood pump and heartbeat signals from a linear combination of the two signals, using (1) filtering, (2) transforms, (3) wavelet techniques, and (4) envelope detector methods. There is much overlap in the frequency domain of the two signals and hence, simple filtering is not effective in separating the two. Although the discrete cosine transform (DCT) achieves energy compactness, the domain of significant support of the heartbeat signal extends beyond that of the blood pump signal. Adaptive modification of the DCT of the combined signal by attenuation of the higher order coefficients and modification of the lower order coefficients can lead to a recovered blood pump signal which can then be subtracted from the combined signal to give the heartbeat. A similar approach is envisioned using the Discrete Hadamard Transform (DHT). In the wavelet domain, the first attempt is to use a Haar wavelet to decompose the combined signal into frequency bands, adaptively alter the wavelet transform coefficients in each band and recover one of the signals. The other signal is obtained by sample by sample subtraction. Finally, if the combined signal represents an amplitude modulated signal it will be demodulated using communication system techniques, such as the proposed envelope detector method, rather than digital signal processing techniques, mentioned above.

Figure 11:
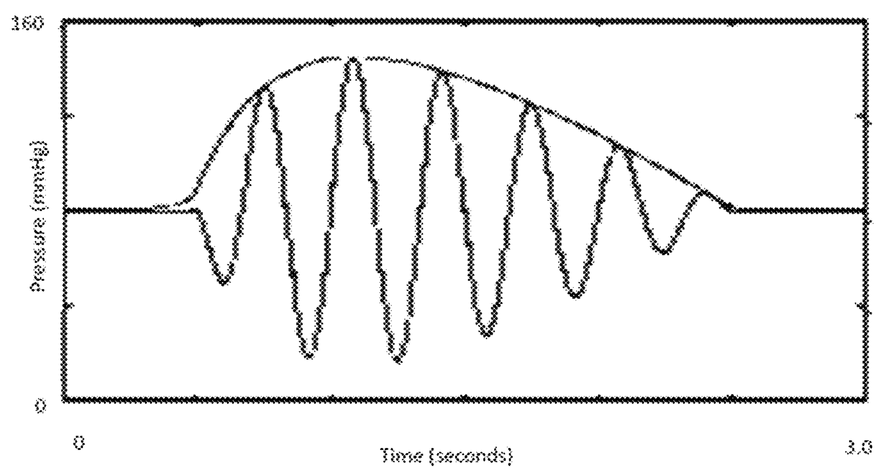
FIG. 11 shows an envelope detection method may filter or parse the signal of interest.
Figure 12:
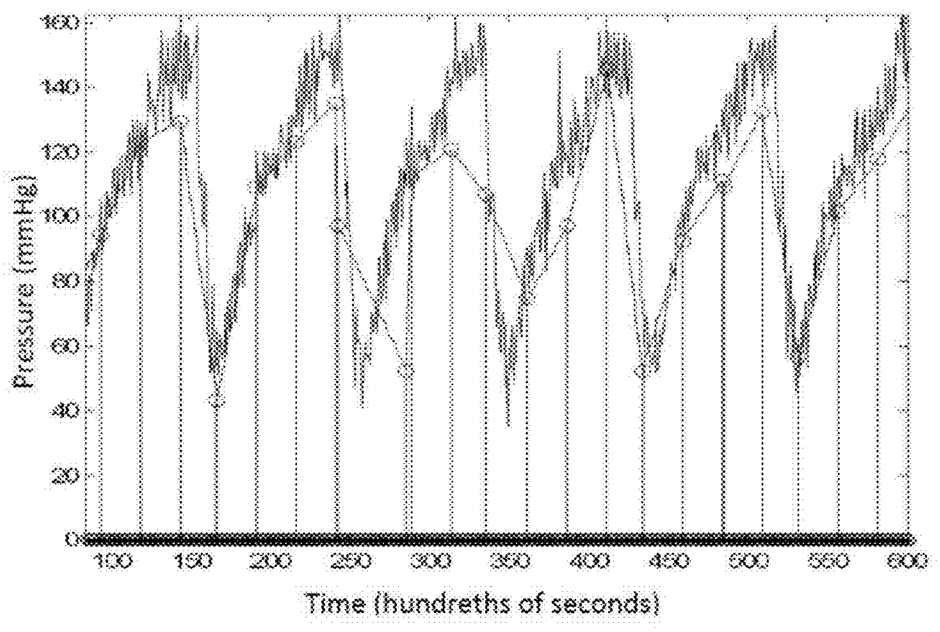
FIG. 12 shows the outcome of a non-limiting example of an envelope detector algorithm.

For the disclosed cooling apparatus, the message (or modulating wave) is the coronary waveform and the carrier is the blood pumping pressure that is introduced by the operation of the cooling apparatus itself. FIG. 10 shows this in detail with the dashed line in FIG. 10C showing an initial estimate of envelope detection. For each of FIGS. 10A-10C, the plots are pressure versus time with time increments of 0.2 seconds. The mean values for pressure are 300 mm Hg for the pump and 100 mm Hg for the heart. Whereas FIG. 11 shows the envelope detection system graphically to exemplify the capabilities of the envelope detections system. FIG. 12 shows the outcome of a non-limiting example of an envelope detection algorithm employed by the control module 6, such as shown in FIG. 13, as an intermediate output using actual blood pump and heart pressures. Blood pressure is plotted as a function of sample measurements at a sampling rate of 100 samples per second. Ultimately this coronary pressure sensing system (CPSS, not shown) ensures the safe and effective operation of the cooling apparatus and a unique attribute of this embodiment.

As an alternative to the envelope detection algorithm, collected pressure data is used by the control module 6 to develop a coronary pressure extraction algorithm, chiefly based on filtering techniques. The measured signal is projected into a predefined space based on basic fluid elements of resistance, compliance, and inductance, where the coronary blood pressure and the external blood pump pressure signals exhibit large separability. Suppressing the blood pump projected components and projecting back into the time domain, in effect filters out the undesired external blood pump signal. The relatively fixed pressure-flow characteristics of the external blood pump can be used to build the orthogonal base-functions that span the projection space, using well known methods such as Empirical Orthogonal Functions. Care is taken in capturing the pump-to-pump and over-time variations exhibited by the external pump. Integrating into the algorithm additional measurements, such as flow rate and/or motor encoder counts, can enhance performance. Finally, fast Fourier transform methods (FFT) may be employed to take advantage of waveform periodicity and ease of implementation.

Referring to FIG. 14, an alternate embodiment of a hub design of a catheter based device 9 is shown, whereby the fluid path travels solely through one catheter hub 12 leaving the other hub available for intervention or whereby inflow can travel through one hub and outflow through another or combinations thereof. The angle a between the catheter hubs 12 can vary from 5-175 degrees, or can be independent to the other hub and only have a common connection at the proximal most tip of the catheter based device 9.

In one embodiment the cooling apparatus of the present disclosure provides the ability to completely block (i.e., obstruct normal blood flow) an artery proximal to the distal end of the catheter, since the cooling apparatus is delivering a flow of replacement fluid and the control system is monitoring fluid flow pressures with a pressure sensor within the distal tip of the catheter to avoid ventricularization and dampening in vessels of the patient's body.

The cooling apparatus disclosed herein redirects fluid from the patient's body or from a reservoir of fluid through the cooling apparatus to adjust or measure the fluid velocity, mean pressure, and pressure differential, and to sufficiently cool the fluid to create the desired tissue temperature within a localized region of the patient when the fluid is delivered. A feedback control system employed by the control module 6 of the cooling apparatus employs localized temperature and pressure measurements to ensure the desired parameters of a localized region of the patient are achieved. With the cooling apparatus of the present disclosure, the flow of fluid can be delivered using a standard catheter system retrofitted with pressure and/or temperature probes at its most distal end. The cooling system of the present disclosure does not impede the use of interventional procedures while in use. Finally, the cooling system can be quickly adjusted by the control module 6 to induce a mild temperature drop or true hypothermia at a specified rate of cooling and can similarly slowly re-warm the localized tissue to normal body temperature taking into account environmental conditions and the effect of the temperature of surrounding tissue. The feedback control loop utilized by the control module 6 provides specific monitoring and control of the localized pressure and temperature pre-, intra-, and post-ischemia.

In one embodiment of the cooling system, a standard catheter can be used and pressure and/or temperature probes can be introduced and placed within the distal region of the catheter to obtain a point in time measurement used to ensure the desired physiological conditions at a localized area in the body and allow the system to adjust. In one non limiting embodiment pressure and/or temperature probes are not used and some other feedback mechanism is used such as manual control, markers, visualization techniques combinations thereof or other mechanisms able to transmit and indication of pressure or temperature back to the user and/or apparatus. In one none limiting embodiment the system does not include a feedback mechanism and settings rely on experimental data, user knowledge or some other method to set the system parameters. Additionally, the cooling system of the present disclosure is able to handle larger fluid volumes as compared to the prior art and can be used not only in localized cooling but also for systemic cooling and adjustment of the patient's temperature. This may be specifically of great consequence in situations where it is desired to adjust the patient systemic temperature. For example, the use of cooling apparatus as a systemic cooling apparatus may be advantageous during long procedures including transplant harvest and implantation.

In one non limiting embodiment of the invention the cooling system can be used in conjunction with cardiac and neuro intervention procedures. Determining the required capacity and rate for localized cooling of the heart and coronary vasculature is not straight forward. Estimates were done using the first law of thermodynamics, $Q=mC(\Delta T/\Delta t)$ where Q is the quantity of heat transferred to or from the object, m is the mass of the object, C is the specific heat of the material the object is composed of, ΔT is the resulting temperature change of the object and Δt is duration of time to achieve the resulting temperature change. Using a 350 g heart and a heat capacity of 3.6 J/° C./g the equations determined a minimal heat transfer capacity of 30 Watts is required to cool the heart approximately 30° C. within 120 seconds. Although the calculations do not account for temperature modification in a dynamic self-regulating system they provided a basis for experimentation. Using a prototype system within a minimum cooling capacity of 30 Watts, animal experimentation was performed. Using the cooling apparatus of the present disclosure, with a catheter placed in the LAD of a 75 Kg swine, a temperature drop of 3-50° C. was observed in the target region border zone with a flow rate of 50 ml/min. of fluid (i.e., blood) cooled to 28-29° C. at the location of an artificially induced obstruction. Under these conditions ischemic and reperfusion injury to the myocardium was reduced by approximately 50% as compared to controls. Nonetheless, directing cooled fluid from the cooling apparatus of the present disclosure into one specific coronary artery may not prove as efficacious and yield an unacceptable risk to the patient as compared to directing the fluid more proximal within the main coronary artery supplying blood to the heart.

The cooling apparatus of the present disclosure is distinguished on its ability to provide optimal placement based on its overall capacity in terms of volume of fluid, velocity, pressure and temperature to achieve optimal results for each specific patient. The cooling apparatus has the functional breath to cool a specific artery within on organ, to perfuse a specific volume of tissue, or an entire organ or tissue mass. Preferably, the cooling apparatus is configured to provide a cooling capacity in the range of 10-150 Watts.

In one non limiting embodiment of the cooling apparatus of the present disclosure is configured for use in conjunction with neurological intervention procedures. Experimental data for use in cardiac intervention provides a basis for determining the requirements for neurological intervention. Total volumetric flow to the brain is estimated at 750 ml/min., with flow rates for localized cooling ranging from 0-200 ml/min. Additionally neurological tissue (i.e., the brain) can be cooled from 0-100° C. at a minimum and even colder temperatures can be tolerated over a cooling period of 0-20 min. depending upon the cooling regime sought.

Benefits of the cooling system of the present disclosure include, but are not limited to, the speed, safety, and accuracy with which localized cooling can be achieved as compared to systemic cooling via external cooling apparatus. The integration of pressure and temperature sensor within the cooling apparatus or as part of the control systems provide physicians real time data on localized or organ blood pressure and temperature regulation pre-, intra- and post-elimination of the obstruction leading to the ischemic event and avoiding ventricularization, and dampening by the integration of a pressure sensor within the distal tip of the catheter.

The unique functional aspect of the cooling system of the present disclosure as compared to prior art include, but are not limited to, the following features: intra procedural tip pressure measurement via signal processing or a distally placed pressure sensor; temperature probes; guide catheters utilizing a polymer with a low heat transfer coefficient, an insulated jacket or liner and/or additional structural integrity to support the volumetric flow rates of cooled fluid and in one non limiting embodiment containing a port for a pressure sensor, temperature sensor and/or combinations thereof. In one embodiment, the bypass loop enables the fluid flow from the pump to bypass the delivery catheter during specific times, automatically or on demand.

It is known that stagnate fluid may create a safety issue leading to thrombus formation where the fluid is blood and a procedural complication where it is necessary to inject contrast media or therapeutic agents into the tissue. In the event a high pressure environment develops the cooling system of the present disclosure incorporates a control system which will automatically divert fluid from an introduction port to a recirculation loop putting the cooling system into a recirculation mode and adjusting the rate of fluid velocity and pressure to guard against the formation of clot and other fluid born obstructions. These automatic safety feature can be controlled automatically, can be overridden by the user, or can placed on full manual control or combinations thereof.

Similarly to the bypass/recirculation option of the apparatus, one non limiting embodiment of the cooling apparatus of the present disclosure contains a fluid purge feature whereby the status of the fluid is monitored (e.g., hemolysis and clot formation as a change in fluid viscosity). If the conditions monitored by the control module indicate a change in the fluid characteristics indicative of damage or change in fluid properties a fluid purge condition would occur purging the fluid from the cooling system. Purge conditions can similarly be activated by the control module under high pressure or temperature conditions whereby it is advantageous to expel some or all of the fluid from the system. In another non limiting embodiment of the apparatus the system has the capability to infuse cold saline into the fluid pathway allowing adjustments to the cooling capacity and adjustment in the viscosity of the cooled fluid. In another non limiting embodiment of the cooling apparatus of the present disclosure contains features to monitor the presence of air within the system and purge or expel the air either automatically or manually.

Those of ordinary skill will recognize that the apparatus of the present disclosure is designed to be used in conjunction with interventional procedures and work in conjunction with existing medical devices used to reestablish normal blood flow, including but not limited to, balloon angioplasty, stenting, the treatment of total occlusions, clot removal, debulking procedures and/or intentional obstructions associated with medical procedures (e.g., surgery). Additionally, the apparatus of the present disclosure is capable of being used in conjunction with surgical procedures where it is advantageous to locally reduce the temperature of an organ or tissue mass. Those of ordinary skill in the art will recognize that the embodiments depicted and described herein are non-limiting and intended to convey the scope of the present disclosure, its uses, and exemplary embodiments. They are not intended to limit the full scope of the invention and its ability to induce localized hypothermia of organs and tissue in a controlled, repeatable and deliberate manner. The description of the use of the apparatus in the arterial system is non-limiting and the apparatus can be used anywhere localized cooling and local hypothermia would serve to reduce the damage to healthy tissue resulting from ischemic events whether intentional (e.g., in conjunction with surgical or therapeutic procedures) or unintentional (e.g., resulting from a blockage to the blood supply or normal function of an organ or tissue mass within the body).

The invention claimed is:

1. A fluid cooling apparatus for the treatment of reperfusion injury and ischemia, comprising:

a control module having a control panel and a control unit;

a pump operatively coupled to the control module;

a heat exchanger operatively coupled to the control module;

a fluid flow loop linking the pump and heat exchanger, said fluid flow loop including a catheter configured to deliver a flow of fluid to a specific location within a patient's body;

a pressure probe monitoring localized pressure within the fluid flow loop, said pressure probe operatively coupled to the control unit;

wherein the pump is configured to move fluid through the flow loop from one location within a patient's body or an external reservoir;

wherein the heat exchanger is configured to cool the fluid within the flow loop; and wherein the control unit is configured with a feedback control to monitor and adjust the pump pressure, the amount of cooling delivered by the heat exchanger, and a localized pressure within the patient's body to overcome ventricularization, resonance, and dampening within the vasculature of the body.

2. The fluid cooling apparatus of claim 1, further comprising a temperature probe operatively coupled to the control module and configured to provide a local temperature at a distal tip of the catheter within the patient's body; and wherein the control unit is further configured with said feedback control to adjust said pump pressure and the amount of cooling delivered by the heat exchanger within the fluid flow loop to achieve a desired localized temperature.

3. The fluid cooling apparatus of claim 2, further comprising a bubble detector operatively coupled to said control module, said bubble detector disposed in direct contact with the fluid flow loop external to the patient; and wherein the control module is further configured to stop the flow of fluid within the fluid flow loop and to signal an alarm upon the detection by the bubble detector of a void or bubble within the portion of the fluid flow loop external to the patient.

4. The fluid cooling apparatus of claim 2 further including a secondary chiller operatively coupled to the fluid flow loop to cool the fluid.

5. The fluid cooling apparatus of claim 2 further including a recirculation shunt and at least one recirculation valve within the fluid flow loop; and wherein said at least one recirculation valve is operatively controlled by the control module to selectively redirect a flow of cooled fluid from the patient into the recirculation shunt to bypass the delivery of cooled fluid to the patient.

6. The fluid cooling apparatus of claim 5 wherein said control module is configured to selectively redirect said flow of cooled fluid in response to a localized pressure within the patient.

7. The fluid cooling apparatus of claim 5 wherein said control module is configured to selectively redirect said flow of cooled fluid in response to a localized temperature within the patient.

8. The fluid cooling apparatus of claim 5 wherein said control module is configured to selectively redirect said flow of cooled fluid in response to the presence of air bubbles within the fluid flow loop.

9. The fluid cooling apparatus of claim 2, further including a viscosity sensor operatively coupled to the control module and disposed for monitoring the viscosity of the fluid within the fluid flow loop; and wherein said control module is further configured to determine a viability of the fluid within the fluid flow loop for infusion into the patient based on a monitored viscosity of said fluid.

10. The fluid cooling apparatus of claim 2, further including a purge mechanism and a purge valve operatively coupled to the fluid flow loop, said purge mechanism and said purge valve operatively controlled by said control module to purge a flow of fluid from the fluid flow loop.

11. The fluid cooling apparatus of claim 10 wherein said control module is configured to control said purge mechanism and said purge valve to purge said flow of fluid from said fluid flow loop in response to a localized pressure within said patient's body.

12. The fluid cooling apparatus of claim 10 wherein said control module is configured to control said purge mechanism and said purge valve to purge said flow of fluid from said fluid flow loop in response to a localized temperature within the patient's body.

13. The fluid cooling apparatus of claim 10 wherein said control module is configured to control said purge mechanism and said purge valve to purge said flow of fluid from said fluid flow loop in response to the presence of a void or bubble within the fluid flow loop.

14. The fluid cooling apparatus of claim 10 wherein said control module is configured to control said purge mechanism and said purge valve to purge said flow of fluid from said fluid flow loop in response to a detected change in viscosity of the fluid indicating an obstruction or clot within the fluid flow loop.

15. The fluid cooling apparatus of claim 1 wherein the pressure probe is located at the exit of the heat exchanger and the control module is configured to processes the pressure signal to decoupling a signal representative of a cardiac pressure level within the patient from a signal representative of a pump pressure within the fluid flow loop; and wherein said signal representative of said cardiac pressure level is representative of a local cardiac pressure at a localized region within the patient.

16. An apparatus for the treatment of reperfusion injury and ischemia, comprising:

a control unit;

a pump operatively connected to the control unit;

a heat exchanger operatively connected to the control unit;

a fluid flow loop providing a fluid flow pathway between the pump and the heat exchanger, said fluid flow loop further including a catheter for fluid communication with a localized region within a patient's body;

a pressure probe monitoring a localized pressure within the fluid flow loop, said pressure probe operatively connected to the control unit;

a temperature probe monitoring a localized temperature within the fluid flow loop, said temperature probe operatively connected to the control unit;

wherein said control unit is configured to direct a flow of fluid through said fluid flow loop to cool said fluid and to create a region of localized hypothermia at said localized region by drawing fluid from a reservoir, cooling the fluid within said heat exchanger to a specific temperature, and delivering said fluid to said localized region by pumping it through said catheter; and wherein said control unit is further configured with an algorithm to identify a localized fluid pressure within the patient's body and to operatively control said pump and said heat exchanger to adjust a rate of fluid delivery, an amount of cooling, said localized pressure, and a localized temperature to overcome heat loss within the catheter and the fluid flow loop distal to the heat exchanger, together with heating from surrounding tissue and organs within the patient's body, to create a localized region of stable hypothermia without over pressurization of the localized area and guarding against ventricularization, resonance, and dampening within associated vasculature.

* * * * *